(12) United States Patent
Greene, Jr. et al.

(10) Patent No.: US 6,299,619 B1
(45) Date of Patent: Oct. 9, 2001

(54) METHODS FOR EMBOLIZING A TARGET VASCULAR SITE

(75) Inventors: George R. Greene, Jr., Costa Mesa; Robert F. Rosenbluth; Brian J. Cox, both of Laguna Niguel, all of CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 09/542,145

(22) Filed: Apr. 4, 2000

Related U.S. Application Data

(63) Continuation-in-part of application No. 09/410,970, filed on Oct. 4, 1999.

(51) Int. Cl.$^7$ ........................................................... A61F 11/00
(52) U.S. Cl. ........................................................... 606/108
(58) Field of Search ..................................... 606/108, 191, 606/194, 195, 200

(56) References Cited

U.S. PATENT DOCUMENTS

| | | |
|---|---|---|
| 3,709,842 | 1/1973 | Stoy et al. . |
| 4,301,803 | 11/1981 | Handa et al. . |
| 4,365,621 | 12/1982 | Brundin . |

(List continued on next page.)

FOREIGN PATENT DOCUMENTS

| | | |
|---|---|---|
| 97/48351 | 12/1997 | (WO) . |
| 99/23954 | 5/1999 | (WO) . |
| 99/56783 | 11/1999 | (WO) . |
| 99/59479 | 11/1999 | (WO) . |

OTHER PUBLICATIONS

Chirila, T. V. et al., "Poly(2–hydroxyethyl methacrylate) sponges as implant materials: in vivo and in vitro evaluation of cellular invasion," *Biomaterials*, 1993, vol. 14 No. 1.

(List continued on next page.)

*Primary Examiner*—Gene Mancene
*Assistant Examiner*—Eduardo C. Robert
(74) *Attorney, Agent, or Firm*—Klein & Szekeres, LLP

(57) ABSTRACT

An embolization device includes a plurality of highly-expansible embolizing elements disposed at spaced intervals along a filamentous carrier. In a preferred embodiment, the carrier is a suitable length of very thin, highly flexible filament of nickel/titanium alloy. The embolizing elements are separated from each other on the carrier by radiopaque spacers in the form of highly flexible microcoils made of platinum or platinum/tungsten alloy. In a preferred embodiment, the embolizing elements are made of a hydrophilic, macroporous, polymeric, hydrogen foam material. The device is particularly suited for embolizing a vascular site such as an aneurysm. The embolization bodies have an initial configuration in the form of small, substantially cylindrical "micropellets" of small enough outside diameter to fit within a microcatheter. The bodies are hydrophilically expansible into an expanded configuration in which they substantially conform to and fill the vascular site while connected to the carrier. A method for embolizing a vascular site using this device includes the steps of: (a) passing a microcatheter intravascularly so that its distal end is in a vascular site; (b) providing a vascular embolization device comprising a plurality of highly expansible embolizing elements carried on a filamentous carrier and separated from each other on the carrier by microcoil spacers; (c) passing the embolization device through the microcatheter so that it emerges from the distal end of the microcatheter into the vascular site; and (d) expanding the embolizing elements in situ substantially to fill the vascular site while retaining the embolizing elements on the carrier. Preferably, the method also includes the step of deploying a vaso-occlusive device in the vascular site, or an intravascular device in a blood vessel adjacent the vascular site, before embolization device is passed through the microcatheter.

19 Claims, 6 Drawing Sheets

U.S. PATENT DOCUMENTS

| | | |
|---|---|---|
| 4,402,319 | 9/1983 | Handa et al. . |
| 4,509,504 | 4/1985 | Brundin . |
| 4,529,739 | 7/1985 | Scott et al. . |
| 4,663,358 | 5/1987 | Hyon et al. . |
| 5,120,349 | 6/1992 | Stewart et al. . |
| 5,122,136 | 6/1992 | Guglielmi et al. . |
| 5,129,180 | 7/1992 | Stewart et al. . |
| 5,226,911 | 7/1993 | Chee et al. . |
| 5,250,071 | 10/1993 | Palermo . |
| 5,258,042 | 11/1993 | Mehta . |
| 5,304,194 | 4/1994 | Chee et al. . |
| 5,312,415 * | 5/1994 | Palermo ............................. 606/108 |
| 5,350,397 | 9/1994 | Palermo et al. . |
| 5,354,290 | 10/1994 | Gross . |
| 5,456,693 | 10/1995 | Conston et al. . |
| 5,541,234 | 7/1996 | Unger et al. . |
| 5,573,994 | 11/1996 | Kabra et al. . |
| 5,582,619 | 12/1996 | Ken . |
| 5,624,461 | 4/1997 | Mariant . |
| 5,624,685 | 4/1997 | Takahashi et al. . |
| 5,645,558 | 7/1997 | Horton . |
| 5,672,634 | 9/1997 | Tseng et al. . |
| 5,690,671 | 11/1997 | McGurk et al. . |
| 5,718,711 | 2/1998 | Berenstein et al. . |
| 5,750,585 | 5/1998 | Park et al. . |
| 5,752,974 | 5/1998 | Rhee et al. . |
| 5,766,160 | 6/1998 | Samson et al. . |
| 5,766,219 | 6/1998 | Horton . |
| 5,823,198 | 10/1998 | Jones et al. . |
| 5,891,155 | 4/1999 | Irie . |
| 5,911,731 | 6/1999 | Pham et al. . |
| 5,916,235 * | 6/1999 | Guglielmi ............................. 606/200 |
| 5,935,148 | 8/1999 | Villar et al. . |
| 5,980,514 | 11/1999 | Kupiecki et al. . |
| 5,980,554 | 11/1999 | Lenker et al. . |
| 6,024,754 | 2/2000 | Engelson . |
| 6,066,149 | 5/2000 | Samson et al. . |
| 6,093,199 | 7/2000 | Brown et al. . |
| 6,113,629 | 9/2000 | Ken . |
| 6,139,520 * | 10/2000 | McCrory et al. ....................... 604/60 |

OTHER PUBLICATIONS

Horák, D. et al., "Hydrogels in endovascular embolization.II,Clinical use of spherical particles," *Biomaterials* (1986), vol. 7, Nov., pp. 467–470.

Horák, D. et al., "New radiopaque polyHEMA–based hydrogel particles," *Journal of Biomedical Materials Research*, vol. 34, pp. 183–188, (1997).

Latchaw, R.E., M.D. et al.., "Polyvinl Foam Embolization of Vascular and Neoplastic Lesions of the Head, Neck and Spine," *Department of Radiology, University of Minnesota Hospitals*, Radiology 131:669–679, Jun.1979.

Vacanti et al., "Tissue Engineering: The Design and Fabrication of Living Replacement Devices for Surgical Reconstruction and Transplantation." *The Lancet* (vol. 354, Supplement 1) pp. 32–34 (Jul., 1999).

Langer, "Tissue Engineering: A new Field and Its Challenges," *Pharmaceutical Research*, vol. 14, No. 7, pp. 840–841 (Jul., 1997).

Persidis, "Tissue engineering," *Nature Biotechnology*, vol. 17, pp. 508–510 (May, 1999).

Zollikofer, Christoph et al., "A Combination of Stainless Steel Coil and Compressed Ivalon: A New Technique for Embolization of Large Arterie and Arteriovenous Fistulas", *Technical Notes*, vol. 138, pp. 229–231, Jan. 1981.

Hogg, Phillip J. et al., "Interaction of platelet–derived growth factor with thrombospondin 1", *Biochem J.*(1997) 326, 709–716.

Larsen, Nancy E. et al., "Hyland gel composition for percutaneous embolization", *Journal of Biomedical Materials Research*, vol. 25, 699–710 (1991).

Soranzo, C. et al., "Evaluation of Two Hyaluronan Derivatives (Hyaff7 and ACP Sponges) For Bone Healing", *The 20th Annual Meeting of the Society for Biomaterials*, Apr. 5–9, 1994, p. 99.

Hoekstra, Djoerd, "Hyaluronan–Modified Surfaces for Medical Devices", *Medical Device & Diagnostic Industry*, Feb. 1999, pp. 48–56.

Woerly, S. et al., "Intracerebral Implantation of Hydrogel–Coupled Adhesion Peptides: Tissue Reaction", *Journal of Neural Transplantation & Plasticity*, vol. 5, No. 4, 1995, pp. 245–255.

Edelman, Elazer R.,"Controlled and modulated release of basic fibroblast growth factor", *Biomaterials*, Sep. 1991, vol. 12, pp. 619–626.

Tadavarthy, S. Murthy et al., "Polyvinyl Alcohol (Ivalon)–A New Embolic Material," *Department of Radiology, University of Minnesota Hospitals*, vol. 125, No. 3, Nov. 1975.

Zollikofer, Christoph et al., "Therapeutic Blockade of Arteries Using Compressed Ivalon[1]", *Department of Radiology, University of Minnesota Hospitals*, Radiology 136:635–640, Sep., 1980.

* cited by examiner

METHODS FOR EMBOLIZING A TARGET VASCULAR SITE

CROSS REFERENCE TO RELATED APPLICATION

This application is a Continuation-in-Part of co-pending application Ser. No. 09/410,970, filed Oct. 4, 1999.

FEDERALLY SPONSORED RESEARCH OR DEVELOPMENT

Not applicable

BACKGROUND OF THE INVENTION

The present invention relates to the field of methods and devices for the embolization of vascular aneurysms and similar vascular abnormalities. More specifically, the present invention relates to an embolic device that is inserted into a vascular site such as an aneurysm to create an embolism therein and a method for embolizing a vascular site using the device.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene vinyl alcohol dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Patents: U.S. Pat. No. 4,551,132—Pásztor et al.; U.S. Pat. No. 4,795,741—Leshchiner et al.; U.S. Pat. No. 5,525,334—Ito et al.; and U.S. Pat. No. 5,580,568—Greffet al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. patents: U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"), described in U.S. Pat. No. 5,122,136—Guglielmi et al. The GDC employs a platinum wire coil fixed to a stainless steel delivery wire by a solder connection. After the coil is placed inside an aneurysm, an electrical current is applied to the delivery wire, which heats sufficiently to melt the solder junction, thereby detaching the coil from the delivery wire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

Still another approach to the embolization of an abnormal vascular site is the injection into the site of a biocompatible hydrogel, such as poly (2-hydroxyethyl methacrylate) ("pHEMA" or "PHEMA"); or a polyvinyl alcohol foam ("PAF"). See, e.g., Horák et al., "Hydrogels in Endovascular Embolization. II. Clinical Use of Spherical Particles",

*Biomaterials*, Vol. 7, pp. 467–470 (November., 1986); Rao et al., "Hydrolysed Microspheres from Cross-Linked Polymethyl Methacrylate", *J. Neuroradiol.*, Vol. 18, pp. 61–69 (1991); Latchaw et al., "Polyvinyl Foam Embolization of Vascular and Neoplastic Lesions of the Head, Neck, and Spine", *Radiology*, Vol. 131, pp. 669–679 (June, 1979). These materials are delivered as microparticles in a carrier fluid that is injected into the vascular site, a process that has proven difficult to control.

A further development has been the formulation of the hydrogel materials into a preformed implant or plug that is installed in the vascular site by means such as a microcatheter. See, e.g., U.S. Pat. No. 5,258,042—Mehta. These types of plugs or implants are primarily designed for obstructing blood flow through a tubular vessel or the neck of an aneurysm, and they are not easily adapted for precise implantation within a sac-shaped vascular structure, such as an aneurysm, so as to fill substantially the entire volume of the structure.

U.S. Pat. No. 5,823,198—Jones et al. discloses an expansible PVA foam plug that is delivered to the interior of an aneurysm at the end of a guidewire. The plug comprises a plurality of pellets or particles that expand into an open-celled structure upon exposure to the fluids within the aneurysm so as to embolize the aneurysm. The pellets are coated with a blood-soluble restraining agent to maintain them in a compressed state and attached to the guidewire until delivered to the aneurysm. Because there is no mechanical connection between the pellets and the guidewire (other than the relatively weak temporary bond provided by the restraining agent), however, premature release and migration of some of the pellets remains a possibility.

There has thus been a long-felt, but as yet unsatisfied need for an aneurysm treatment device and method that can substantially fill aneurysms of a large range of sizes, configurations, and neck widths with a thrombogenic medium with a minimal risk of inadvertent aneurysm rupture or blood vessel wall damage. There has been a further need for such a method and device that also allow for the precise locational deployment of the medium, while also minimizing the potential for migration away from the target location. In addition, a method and device meeting these criteria should also be relatively easy to use in a clinical setting. Such ease of use, for example, should preferably include a provision for good visualization of the device during and after deployment in an aneurysm.

SUMMARY OF THE INVENTION

Broadly, an embolization device, according to a first aspect of the present invention, comprises one or more expansible, hydrophilic embolizing elements non-releasably carried on a filamentous carrier at spaced intervals along the length of the carrier. In a preferred embodiment, the carrier is a suitable length of very thin, highly flexible filament of nickel/titanium alloy. The embolizing elements are separated from each other on the carrier by radiopaque spacers in the form of highly flexible microcoils made of platinum or platinum/tungsten alloy, as in the thrombogenic microcoils of the prior art, as described above.

In a preferred embodiment, the embolizing elements are made of a hydrophilic, macroporous, polymeric, hydrogel foam material, in particular a swellable foam matrix formed as a macroporous solid comprising a foam stabilizing agent and a polymer or copolymer of a free radical polymerizable hydrophilic olefm monomer cross-linked with up to about 10% by weight of a multiolefin-functional cross-linking agent. Such a material is described in U.S. Pat. No. 5,750,585—Park et al., the disclosure of which is incorporated herein by reference. The material may be modified, or provided with additives, to make the implant visible by conventional imaging techniques.

A second aspect of the present invention is a method for embolizing a vascular site, comprising, in the preferred embodiment the steps of: (a) passing a microcatheter intravascularly so that its distal end is introduced into a target vascular site; (b) passing a vaso-occlusive device through the microcatheter into the target vascular site so that the vaso-occlusive device assumes a three-dimensional configuration that fills a portion of the volume of the target vascular site; (c) providing a vascular embolization device comprising at least one expansible embolizing element non-releasably connected to a filamentous carrier; (d) passing the embolization device through the microcatheter so that it emerges from the distal end of the microcatheter into the target vascular site; and (e) expanding the embolizing element or elements in situ substantially to fill the remaining volume of the target vascular site while maintaining the connection between the embolizing element or elements and the carrier.

Preferably, the vaso-occlusive device is of the type that is initially in the form of an elongate, flexible, filamentous element for delivery through the microcatheter, and that assumes a three-dimensional geometry upon installation in the target vascular site. One such device is the above-described GDC (U.S. Pat. No. 5,122,136—Guglielmi et al., the disclosure of which is incorporated herein by reference). Other such devices are describe in, for example, U.S. Pat. No. 5,766,219—Horton; U.S. Pat. No. 5,690,671—McGurk et al.; and U.S. Pat. No. 5,911,731—Pham et al., the disclosures of which are incorporated herein by reference. Still other types of vaso-occlusive devices known in the art may also perform satisfactorily in this method.

In an alternative embodiment of the method of the present invention, the method comprises the steps of: (a) deploying an intravascular device to a position in a blood vessel adjacent to a target vascular site; (b) providing a vascular embolization device comprising at least one expansible embolizing element non-releasably connected to a filamentous carrier; (c) passing a microcatheter intravascularly so that the distal end of the microcatheter passes through the intravascular device into the target vascular site; (d) passing the embolization device through the microcatheter so that it emerges from the distal end of the microcatheter into the target vascular site; and (e) expanding the embolizing element or elements in situ substantially to fill the volume of the target vascular site while maintaining the connection between the embolizing element or elements and the carrier.

It is understood that the step of providing the embolization device may follow the step of passing the microcatheter intravascularly.

In this alternative embodiment, the intravascular device may be of the type disclosed in U.S. Pat. No. 5,980,514—Kupiecki et al., the disclosure of which is incorporated herein by reference. This intravascular device comprises a filamentous element that is introduced by a microcatheter to the juncture of an aneurysm or the like, and that then assumes the configuration of a coil adjacent the neck of the aneurysm.

In some instances, the step of passing a vaso-occlusive device or an intravascular device through the microcatheter to the target vascular site may be omitted.

The embolization bodies or elements, in the preferred embodiment, have an initial configuration in the form of small, substantially cylindrical "micropellets" of small enough outside diameter to fit within the microcatheter. The bodies are hydrophilically expansible into an expanded configuration in which they substantially conform to and fill the vascular site.

The present invention provides a number of significant advantages. Specifically, the present invention provides an effective vascular embolization device that can be deployed within a vascular site with excellent locational control, and with a lower risk of vascular rupture, tissue damage, or migration than with prior art devices. Furthermore, the embolization device effects a conformal fit within the site that promotes effective embolization, and yet its ability to be delivered to the site through a microcatheter facilitates precise and highly controllable deployment. In addition, the essentially filamentous initial configuration of the embolization device, whereby it readily conforms to the interior dimensions of the vascular site, allows it to be used effectively to embolize vascular sites having a wide variety of sizes, configurations, and (in the particular case of aneurysms) neck widths. These and other advantages will be readily appreciated from the detailed description that follows.

DETAILED DESCRIPTION OF THE INVENTION

The Embolization Device.

Figure 1:
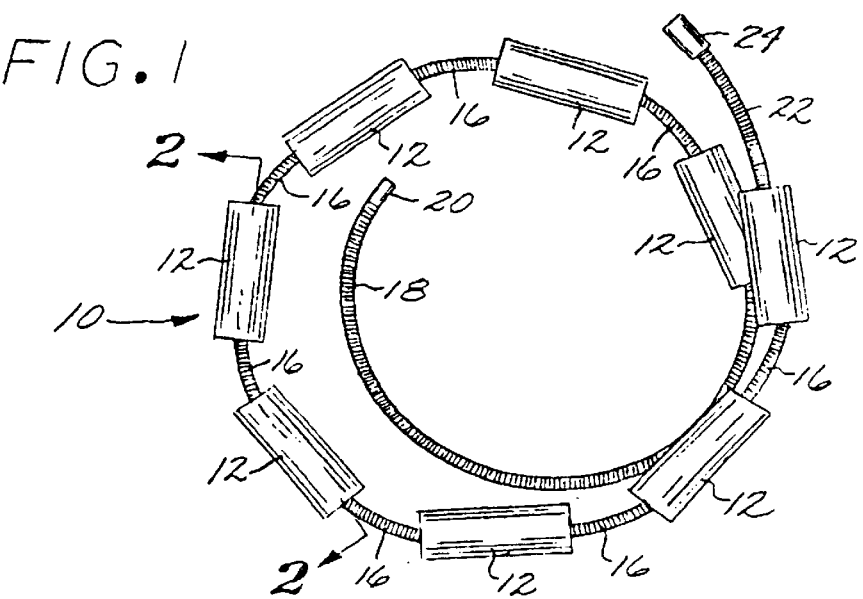
FIG. 1 is an elevational view of a vascular embolization device in accordance with a preferred embodiment of the invention.
Figure 2:
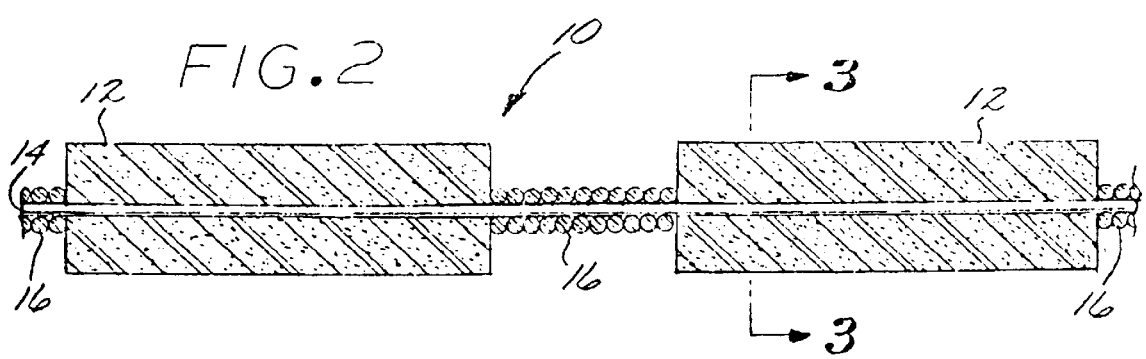
FIG. 2 is a cross-sectional view taken along line 2—2 of FIG. 1.
Figure 3:
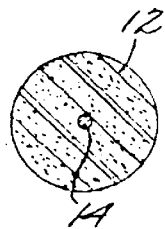
FIG. 3 is a cross-sectional view taken along line 3—3 of FIG. 2.

A vascular embolization device 10, in accordance with the present invention, is shown in FIGS. 1, 2 and 3. In the preferred embodiment, the embolization device 10 comprises a plurality of embolizing bodies, each configured as a substantially cylindrical "micropellet" 12, located at spaced intervals along a filamentous carrier 14. The number of micropellets 12 will vary, depending on the length of the carrier 14, which, turn, will depend on the size of the vascular site to be embolized. For a large vascular site, for example, eight to twelve micropellets may be used, although an even larger number may be used if necessary. In some applications (e.g., very small aneurysms), as few as one or two micropellets may be used.

Also carried on the carrier 14 is a plurality of highly flexible microcoil spacers 16, each of which is disposed between and separates a pair of micropellets 12. The carrier 14 has a distal portion on which is carried a relatively long distal microcoil segment 18 that is retained in place by a distal retention member 20. The carrier 14 has a proximal portion on which is carried a relatively long proximal microcoil segment 22. The proximal end of the device 10 is terminated by a hydrogel linkage element 24, to be described below. The spacers 16, the distal microcoil segment 18, and the proximal microcoil segment 22 are all highly flexible, and they are preferably made of platinum or platinum/tungsten wire, which has the advantages of being biocompatible and radiopaque. The micropellets 12 are non-releasably carried on the carrier 14. They may be fixed in place on the filamentous carrier 14, either mechanically or by a suitable biocompatible, water-insoluble adhesive, or they may be simply strung loosely on the carrier 14 between successive spacers 16.

The micropellets 12 are preferably formed of a biocompatible, macroporous, hydrophilic hydrogel foam material, in particular a water-swellable foam matrix formed as a macroporous solid comprising a foam stabilizing agent and a polymer or copolymer of a free radical polymerizable hydrophilic olefin monomer cross-linked with up to about 10% by weight of a multiolefm-functional cross-linking agent. A suitable material of this type is described in U.S. Pat. No. 5,570,585—Park et al., the disclosure of which is incorporated herein by reference.

Another suitable material for the micropellets 12 is a porous hydrated polyvinyl alcohol (PVA) foam gel prepared from a polyvinyl alcohol solution in a mixed solvent consisting of water and a watermiscible organic solvent, as described, for example, in U.S. Pat. No. 4,663,358—Hyon et al., the disclosure of which is incorporated herein by reference. Other suitable PVA structures are described in U.S. Pat. No. 5,823,198—Jones et al. and U.S. Pat. No. 5,258,042—Mehta, the disclosures of which are incorporated herein by reference. Another suitable material is a collagen foam, of the type described in U.S. Pat. No. 5,456,693—Conston et al., the disclosure of which is incorporated herein by reference. Still another suitable material is PHEMA, as discussed in the references cited above. See, e.g., Horák et al., supra, and Rao et al., supra.

The preferred foam material, as described in the above-referenced patent to Park et al., has a void ratio of at least about 90%, and its hydrophilic properties are such that it has a water content of at least about 90% when fully hydrated. In the preferred embodiment, each of the embolizing micropellets 12 has an initial diameter of not more than about 0.5 mm prior to expansion in situ, with an expanded diameter of at least about 3 mm. To achieve such a small size, the micropellets 12 may be compressed to the desired size from a significantly larger initial configuration. The compression is performed by squeezing or crimping the micropellets 12 in a suitable implement or fixture, and then "setting" them in the compressed configuration by heating and/or drying. Each of the micropellets 12 is swellable or expansible to many times (at least about 25 times, preferably about 70 times, and up to about 100 times) its initial (compressed) volume, primarily by the hydrophilic absorption of water molecules from an aqueous solution (e.g., resident blood plasma and/or injected saline solution), and secondarily by the filling of its pores with blood. Also, the micropellets 12 may be coated with a water-soluble coating (not shown), such as a starch, to provide a time-delayed expansion. Another alternative is to coat the micropellets 12 with a temperature-sensitive coating that disintegrates in response to normal human body temperature. See, e.g., U.S. Pat. No. 5,120,349—Stewart et al. and U.S. Pat. No. 5,129,180—Stewart.

The foam material of the embolizing micropellet 12 may advantageously be modified, or provided with additives, to make the device 10 visible by conventional imaging techniques. For example, the foam can be impregnated with a water-insoluble radiopaque material such as barium sulfate, as described by Thanoo et al., "Radiopaque Hydrogel Microspheres", *J. Microencapsuladon*, Vol. 6, No. 2, pp. 233–244 (1989). Alternatively, the hydrogel monomers can be copolymerized with radiopaque materials, as described in Horák et al., "New Radiopaque PolyHEMA-Based Hydrogel Particles", *J. Biomedical Matenals Research*, Vol. 34, pp. 183–188 (1997).

The micropellets 12 may optionally include bioactive or therapeutic agents to promote thrombosis, cellular ingrowth, and/or epithelialization. See, e.g, Vacanti et al., "Tissue Engineering: The Design and Fabrication of Living Replacement Devices for Surgical Reconstruction and Transplantation," *The Lancet* (Vol. 354, Supplement 1), pp. 32–34 (July, 1999); Langer, "Tissue Engineering: A New Field and Its Challenges," *Phamaceutical Research*, Vol. 14., No. 7, pp. 840–841 (July, 1997); Persidis, "Tissue Engineering," *Nature Biotechnology*, Vol. 17, pp. 508–510 (May, 1999).

The filamentous carrier 14 is preferably a length of nickel/titanium wire, such as that marketed under the trade name "Nitinol". Wire of this alloy is highly flexible, and it has an excellent "elastic memory", whereby it can be formed into a desired shape to which it will return when it is deformed. In a preferred embodiment of the invention, the wire that forms the carrier 14 has a diameter of approximately 0.04 mm, and it is heat-treated to form a multi-looped structure that may assume a variety of three-dimensional shapes, such as a helix, a sphere, or an ovoid (as disclosed, for example, in U.S. Pat. No. 5,766,219—Horton, the disclosure of which is incorporated herein by rerefence). Preferably, the intermediate portion of the carrier 14 (i.e., the portion that includes the micropellets 12) and the proximal portion (that carries the proximal microcoil segment 22) are formed into loops having a diameter of approximately 6 mm, while the distal portion (that carries the distal microcoil segment 18) may have a somewhat greater diameter (e.g., approximately 8–10 mm). The carrier 14 may be formed of a single wire, or it may be formed of a cable or braided structure of several ultra-thin wires.

In another embodiment, the carrier 14 may be made of a thin filament of a suitable polymer, such as a PVA, that is formed in a looped structure. The polymer may be impregnated with a radiopaque material (e.g., barium sulfate particles of gold, tantalum, or platinum), or it may enclose a core of nickel/titanium wire. Alternatively, the carrier 14 may be constructed as a "cable" of thin polymer fibers that includes fibers of an expansile polymer, such as polyvinyl alcohol (PVA), at spaced intervals to form the micropellets 12.

Still another alternative construction for the carrier 14 is a continuous length of microcoil. In such an embodiment, the micropellets 12 would be attached at spaced intervals along the length of the carrier 14.

Figure 8:
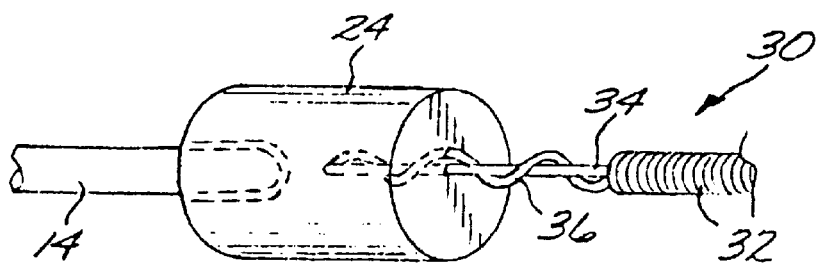
FIG. 8 is a detailed perspective view of mechanism by which the embolization device of the present invention is preferably attached to the distal end of a deployment instrument.
Figure 9:
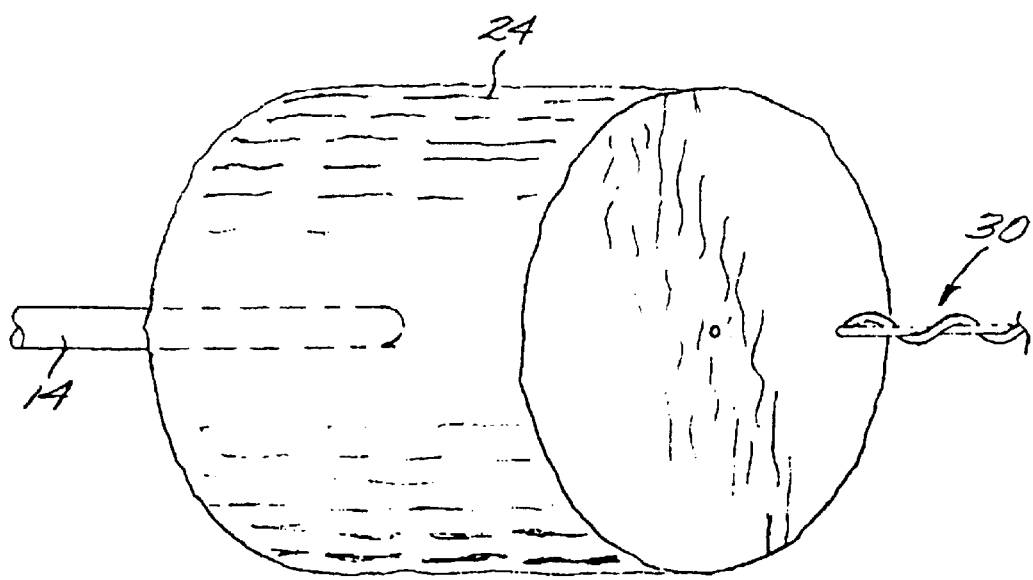
FIG. 9 is a detailed perspective view, similar to that of FIG. 8, showing the embolization device of the present invention after it has been separated from the deployment instrument.

As shown in FIGS. 1, 8, and 9, the hydrogel linkage element 24 is advantageously made of the same material as the micropellets 12. Indeed, the most proximal of the micropellets 12 may function as the linkage element 24. The linkage element 24 is attached to the proximal end of the carrier 14 by a suitable biocompatible adhesive. The purpose of the linkage element 24 is to removably attach the device 10 to a deployment instrument 30 (FIGS. 8 and 9). The deployment instrument 30 comprises a length of platinum or platinum/tungsten microcoil outer portion 32 with a flexible wire core 34 of the same or a similar metal. The deployment instrument 30 has a distal portion 36 at which the microcoil outer portion 32 has coils that are more distantly-spaced (i.e., have a greater pitch).

As shown in FIG. 8, the device 10 is initially attached to the deployment instrument 30 by means of the linkage element 24. Specifically, the linkage element 24 is installed, in a compressed state, so that it encompasses and engages both the proximal end of the embolization device 10 and the distal portion 36 of the deployment instrument 30. Thus, in the compressed state, the linkage element 24 binds the deployment instrument 30 and the embolization device 10 together. As shown in FIG. 9, and as will be described in detail below, after the device 10 is deployed in a vascular site, the linkage element 24 expands greatly, thereby loosening its grip on the distal portion 36 of the deployment instrument 30, and thus allowing the embolization device 10 to be separated from the deployment instrument 30 by pulling the latter proximally out of and away from the linkage element 24.

The Method for Embolizing a Vascular Site.

Figure 4:
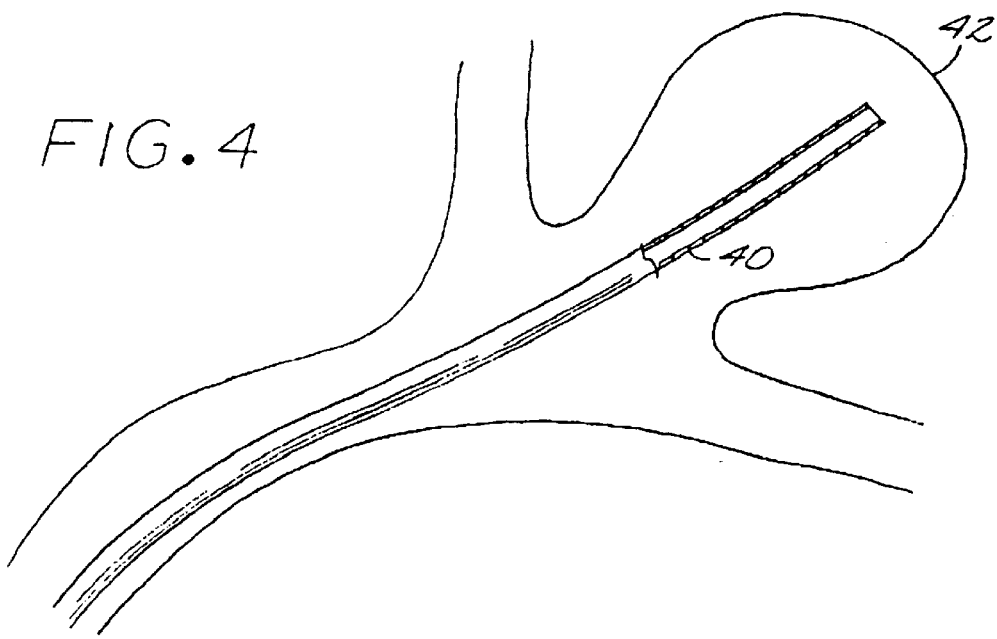
FIGS. 4 through 7 are semischematic views showing the steps in a method of embolizing a vascular site (specifically, an aneurysm) in accordance with one embodiment of the embolizing method aspect of the present invention.
Figure 5:
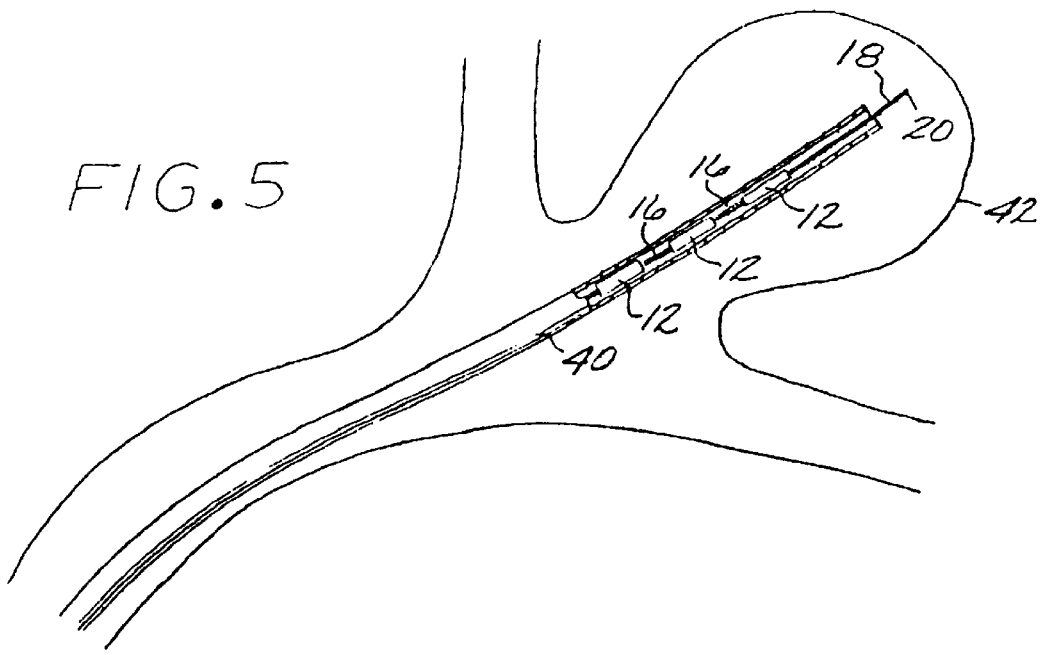
Figure 6:
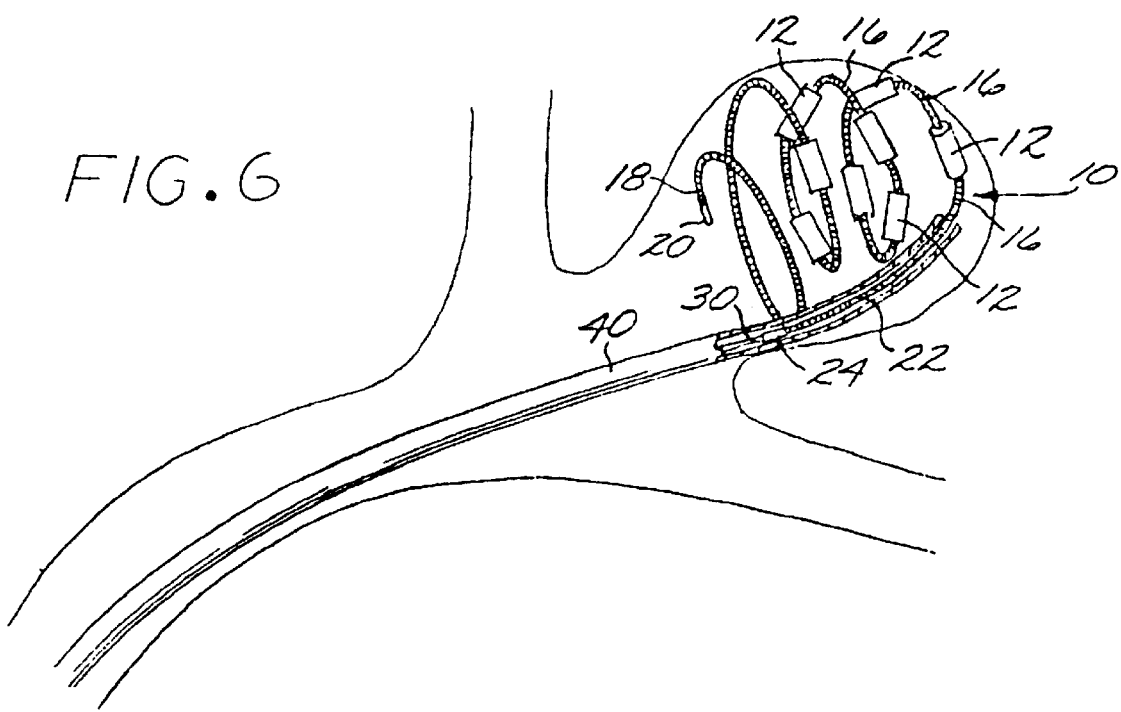

One method of embolizing a vascular site using the embolization device 10 is illustrated in FIGS. 4 through 7. First, as shown in FIG. 4, a microcatheter 40 is threaded intravascularly, by known methods, until its distal end is located within the targeted vascular site (here, an aneurysm 42). Briefly described, this threading operation is typically performed by first introducing a catheter guidewire (not shown) along the desired microcatheter path, and then feeding the microcatheter 40 over the catheter guidewire until the microcatheter 40 is positioned adjacent the distal aspect of the dome of the aneurysm, as shown in FIG. 4. The catheter guidewire is then removed. Then, as shown in FIGS. 5 and 6, the embolization device 10, which is attached to the distal end of the deployment instrument 30, as described above, is passed axially through the microcatheter 40, using the deployment instrument 30 to push the device 10 through the microcatheter 40 until the device 10 is clear from the distal end of the microcatheter 40 and fully deployed within the aneurysm 42 (FIG. 6), filling the aneurysm from its distal aspect. The deployment procedure is facilitated by the visualization of the embolization device 10 that is readily accomplished due to its radiopaque components, as described above.

The embolization bodies or micropellets 12, in their compressed configuration, have a maximum outside diameter that is less than the inside diameter of the microcatheter 40, so that the embolization device 10 can be passed through the microcatheter 40. The micropellets 12 are preferably compressed and "set", as described above, before the device 10 is inserted into the microcatheter 40. When inserting the device 10 into the microcatheter 40, a biocompatible, substantially non-aqueous fluid, such as polyethylene glycol, may be injected into the microcatheter 40 to prevent premature expansion of the device 10 due to hydration, and to reduce friction with the interior of the microcatheter 40.

As shown in FIG. 6, when the embolization device 10 is exposed from the microcatheter 40 into the interior of the vascular site 42, the pores of the embolizing bodies or micropellets 12, and of the linkage element 22, begin to absorb aqueous fluid from the blood within the vascular site 42 to release their "set", allowing these elements to begin assuming their expanded configuration. The expansion can be enhanced and accelerated by injecting saline solution through the microcatheter 40. The expansion of the linkage element 24 allows the embolization device 10 to be separated from the deployment instrument 30, as described above, and the deployment instrument 30 can then be removed. Also, the elastic memory of the carrier 14 causes it to resume its original looped configuration once it is released from the confines of the microcatheter 40. Thus, almost immediately upon its release into the vascular site (aneurysm) 42, the embolization device begins to occupy a significant portion of the volume of the aneurysm 42.

Figure 7:
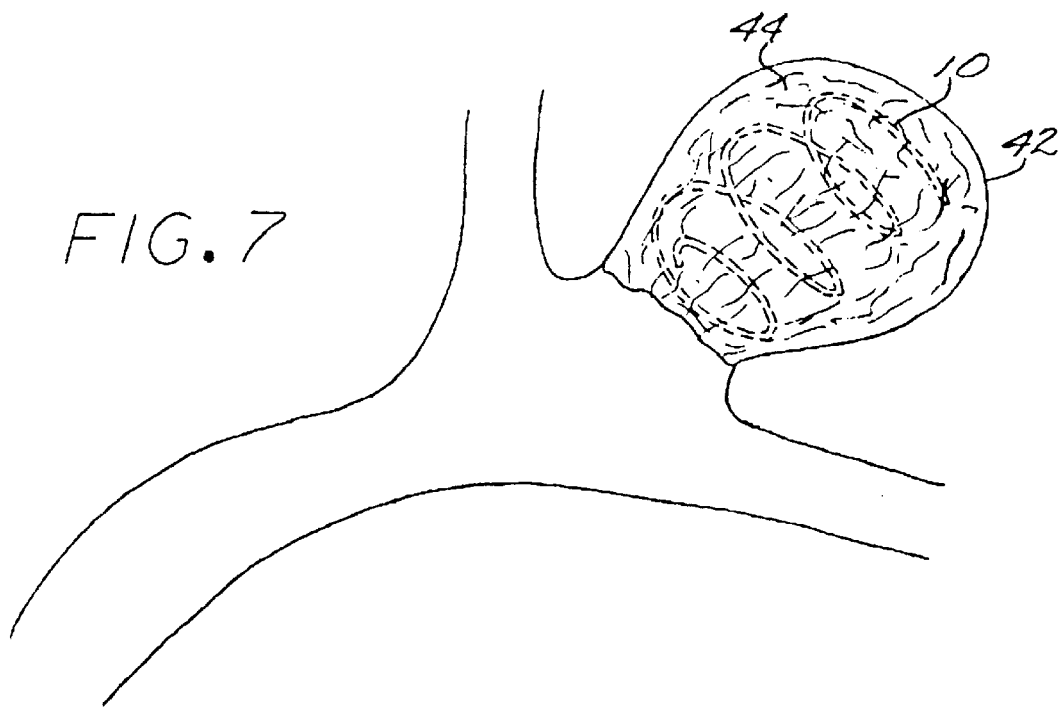

If the micropellets 12 are of a hydrophilic material, they then continue to expand in situ due to hydrophilic hydration of the material, as well as from the filling of their pores with blood. If the embolizing bodies 12 are of a non-hydrophilic material, their expansion is due to the latter mechanism only. In either case, the result, as shown in FIG. 7, is the substantially complete filling of the interior of the aneurysm 42 with the expanded embolizing bodies or micropellets 12, whereby a substantially conformal embolizing implant 44 is formed that substantially fills the interior of the aneurysm 42. The micropellets 12, being non-releasably carried the carrier 14 and fixed in place thereon, stay on the carrier during their expansion. Thus, the chance of a micropellet separating from the carrier and migrating out of the vascular site is minimized.

It may be advantageous, prior to performing the procedural steps described above, preliminarily to visualize the aneurysm 42, by conventional means, to obtain a measurement (or at least an approximation) of its volume. Then, a device 10 of the appropriate size can be selected that would expand to fill the measured or estimated volume.

Figure 10:
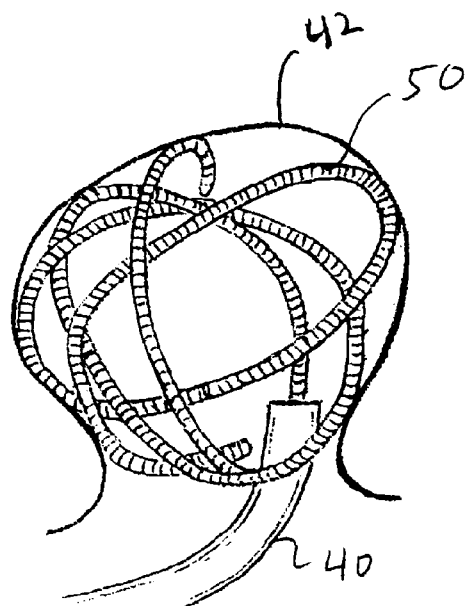
FIGS. 10, 11, and 12 are semischematic views showing steps that, in addition to those illustrated in FIGS. 4–7, constitute a method of embolizing a vascular site in accordance with a preferred embodiment of the embolizing method aspect of the present invention.
Figure 11:
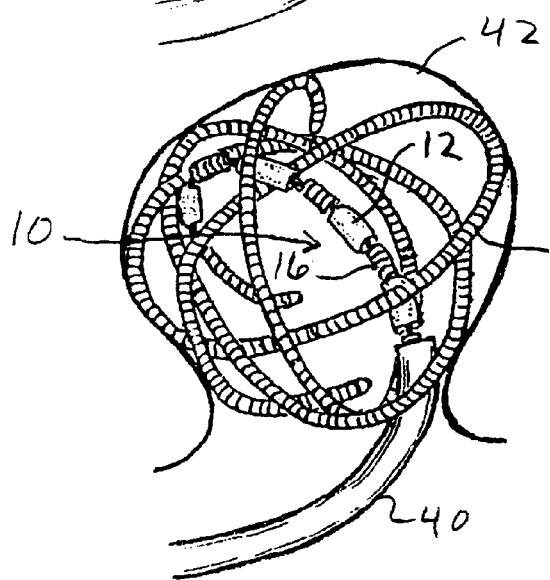
Figure 12:
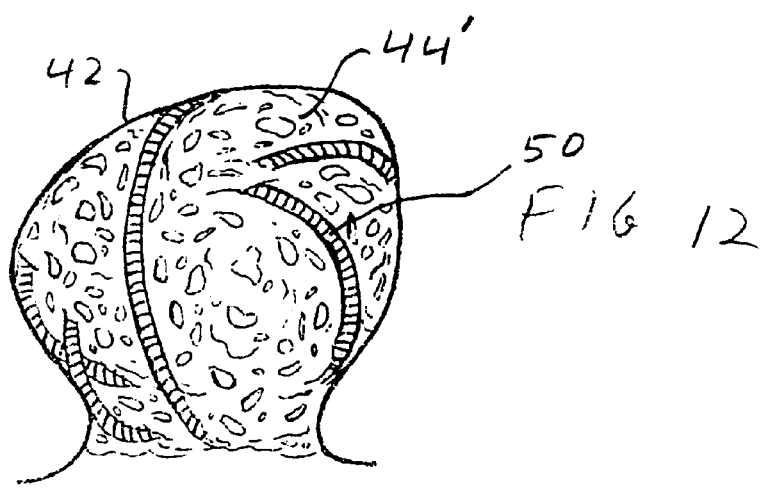

A preferred method of embolizing a target vascular site using the embolization device 10 will be understood with reference to FIGS. 10–12, along with FIGS. 4–7 (discussed above). In this preferred embodiment of the method, the passing of a microcatheter 40 intravascularly until its distal end is introduced into a target vascular site (FIG. 4) is followed by the step of passing a vaso-occlusive device 50 through the microcatheter 40 into the target vascular site (e.g., the aneurysm 42) so that the vaso-occlusive device 50 assumes a three-dimensional configuration that fills a portion of the interior volume of the target vascular site 42, as shown in FIG. 10. The deployed vaso-occlusive device 50 forms a "cage" within the aneurysm 42 that provides a matrix for improved retention of the expansible embolizing bodies or micropellets 12 of the embolization device 10. The embolization device 10 is then passed through the microcatheter 40, as described above, and as shown in FIG. 11, to enter the aneurysm 42 within the voids left by the vaso-occlusive device 50. Finally, the embolizing bodies or micropellets 12 are expanded, as described above, and as shown in FIG. 12, whereby a substantially conformal embolizing implant 44' is formed that substantially fills the remaining interior volume of the aneurysm 42.

Preferably, the vaso-occlusive device 50 is of the type that is initially in the form of an elongate, flexible, filamentous element for delivery through the microcatheter, and that assumes a three-dimensional geometry (either by elastic behavior or by shape memory) upon installation in the target vascular site. Such devices are describe in, for example, U.S. Pat. Nos. 5,122,136—Guglielmi et al.; U.S. Pat. No. 5,766,219—Horton; U.S. Pat. No. 5,690,671—McGurk et al.; and U.S. Pat. No. 5,911,731—Pham et al., the disclosures of which are incorporated herein by reference. Still other types of vaso-occlusive devices known in the art may also perform satisfactorily in this method. For example, a stent-like device like that shown in U.S. Pat. No. 5,980,554—Lenker et al. may be employed Alternatively, the vaso-occlusive device 50 may be designed or installed only to enter the space near the opening or "neck" of the aneurysm. In any case, the purpose of the vaso-occlusive device 50 in this method is to present a structural framework that helps retain the embolization device 10 in place within the target vascular site.

Figure 13:
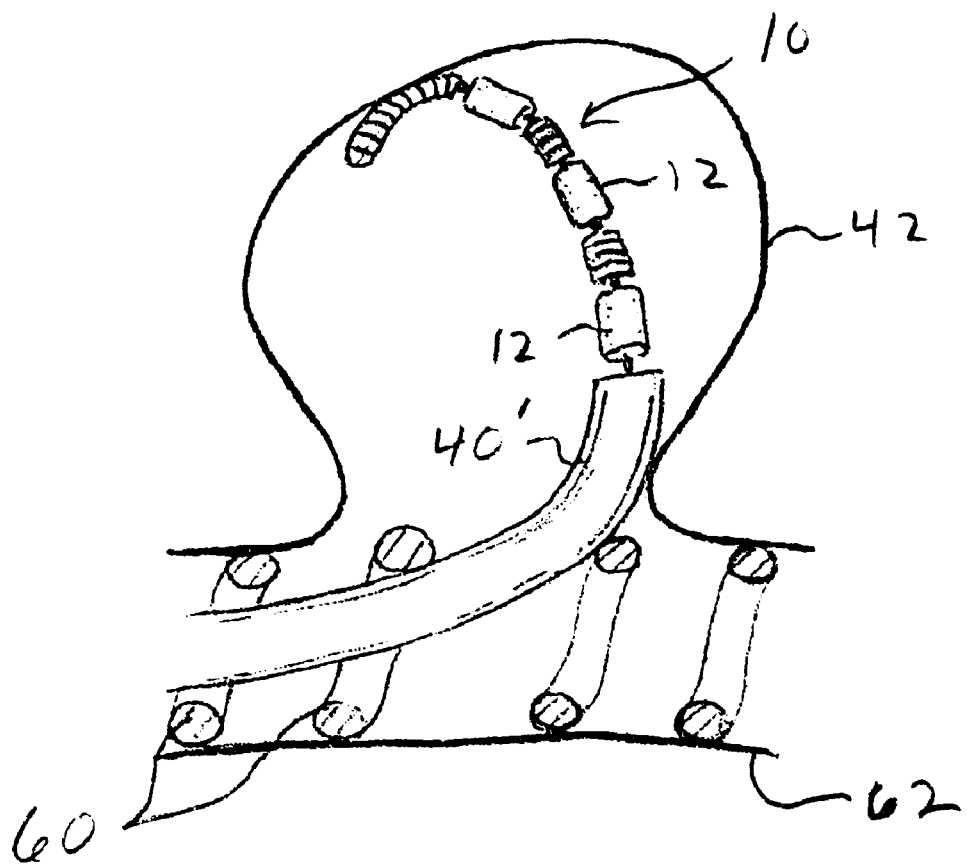
FIG. 13 is a semischematic view showing a step in a method of embolizing a vascular site in accordance with an alternative embodiment of the embolizing method aspect of the present invention.

An alternative embodiment of the method of the present invention will be understood with reference to FIG. 13. In this alternative embodiment, the method includes the preliminary step of deploying an intravascular device 60 to a position in a blood vessel 62 adjacent to a target vascular site 42. A microcatheter 40' is passed intravascularly so that its distal end passes through the intravascular device 60 into the target vascular site 42. The embolization device 10 is passed through the microcatheter 40' so that it emerges from the distal end of the microcatheter 40' into the target vascular site 42, and the embolizing elements 12 are then expanded in situ, as described above, substantially to fill the volume of the target vascular site 42 (as shown in FIGS. 7 and 12).

It is understood that the step of deploying an intravascular device to a position in a blood vessel adjacent to a target vascular site would include any substeps necessary for such deployment. For example, if the intravascular device 60 is of the type disclosed in U.S. Pat. No. 5,980,514—Kupiecki et al. (the disclosure of which is incorporated herein by reference), the deployment step would comprise the substeps of (i) passing of a microcatheter intravascularly so that its distal end is located adjacent the target vascular site; (ii) passing the intravascular device through the microcatheter until it emerges from the distal end of the microcatheter; and (iii) allowing the intravascular device to assume a three-dimensional configuration adjacent to the target vascular site. In this case, either the microcatheter used for deploying the intravascular device could be removed and then another microcatheter used to install the embolization device, or the intravascular deployment microcatheter could be repositioned for the introduction of the embolization device.

In this alternative method, the intravascular device presents an obstruction that at least partially blocks the juncture between the target vascular site and the blood vessel (e.g., the neck of an aneurysm). Thus, the intravascular device helps retain the embolization device in its proper position within the target vascular site.

Although the device 10 has been described above for use in embolizing aneurysms, other applications will readily suggest themselves. For example, it can be used to treat a wide range of vascular anomalies, such as arteriovenous malformations and arteriovenous fistulas. Certain tumors may also be treated by the embolization of vascular spaces or other soft tissue voids using the present invention.

While a preferred embodiment of the invention has been described above, a number of variations and modifications may suggest themselves to those skilled in the pertinent arts. For example, the initial shape and number of embolizing bodies 12 may be varied, as well as the length of the carrier 14. Furthermore, other mechanisms may be found for removably attaching the embolization device 10 to the deployment wire. One such alternative attachment mechanism may be a transition polymer joint that loosens when heated by contact with blood or by a low-level electric current. These and other variations and modifications are considered within the spirit and scope of the invention, as described in the claims that follow.

What is claimed is:

1. A method for embolizing a target vascular site having a defined volume, comprising the steps of:
    (a) passing a microcatheter intravascularly so that its distal end is introduced into a target vascular site;
    (b) passing a vaso-occlusive device through the microcatheter into the target vascular site so that the vaso-occlusive device assumes a three-dimensional configuration that fills a portion of the volume of the target vascular site;
    (c) providing a vascular embolization device comprising an expansible embolizing element non-releasably carried on a flexible filamentous carrier;
    (d) passing the embolization device through the microcatheter so that it emerges from the distal end of the microcatheter into the target vascular site; and
    (e) expanding the embolizing element in situ substantially to fill remaining volume of the target vascular site while retaining the embolizing element on the carrier.

2. The method of claim 1, wherein the step of providing a vascular embolization device includes the steps of:
    (c)(1) determining at least an approximation of the volume of the vascular site; and
    (c)(2) selecting a vascular embolization device sized substantially to fill the volume of the vascular site after the expanding step.

3. The method of claim 2, wherein the step of determining at least the approximate volume of the vascular site includes the step of visualizing the vascular site prior to or during the step of passing the microcatheter intravascularly.

4. The method of claim 1, wherein the expanding step includes the step of passing saline solution through the microcatheter and into the vascular site.

5. The method of claim 1, wherein the step of passing the embolization device through the microcatheter includes the step of injecting a substantially non-aqueous fluid through the microcatheter to prevent hydration of the expansible elements within the microcatheter.

6. The method of claim 5, wherein the non-aqueous fluid is polyethylene glycol.

7. A method of embolizing a target vascular site having a defined volume, comprising the steps of:
    (a) deploying an intravascular device to a position in a blood vessel adjacent to a target vascular site;
    (b) providing a vascular embolization device comprising an expansible embolizing element non-releasably carried on a filamentous carrier;
    (c) passing a microcatheter intravascularly so that the microcatheter passes through the intravascular device into the target vascular site;
    (d) passing the embolization device through the microcatheter so that it emerges from the microcatheter into the target vascular site; and
    (e) expanding the embolizing element in situ substantially to fill the volume of the target vascular site while retaining the embolizing element on the carrier.

8. The method of claim 7, wherein the microcatheter has a distal end, and wherein the step of deploying comprises the steps of:
    (a)(1) passing a microcatheter intravascularly so that its distal end is positioned in a blood vessel adjacent to a target vascular site; and
    (a)(2) passing an intravascular device through the microcatheter so that the intravascular device emerges from the distal end of the microcatheter and assumes a three-dimensional configuration adjacent to the target vascular site.

9. The method of claim 7, wherein the step of providing a vascular embolization device includes the steps of:
    (b)(1) determining at least an approximation of the volume of the vascular site; and
    (b)(2) selecting a vascular embolization device sized substantially to fill the volume of the vascular site after the expanding step.

10. The method of claim 9, wherein the step of determining at least the approximate volume of the vascular site includes the step of visualizing the vascular site prior to or during the step of passing the microcatheter intravascularly.

11. The method of claim 7, wherein the expanding step includes the step of passing saline solution through the microcatheter and into the vascular site.

12. The method of claim 7, wherein the step of passing the embolization device through the microcatheter includes the step of injecting a substantially non-aqueous fluid through the microcatheter to prevent hydration of the expansible elements within the microcatheter.

13. The method of claim 12, wherein the non-aqueous fluid is polyethylene glycol.

14. A method of embolizing a target vascular site having a defined volume, comprising the steps of:
    (a) deploying an intravascular device to a position in a blood vessel adjacent to a target vascular site;
    (b) providing a vascular embolization device comprising an expansible embolizing element non-releasably carried on a filamentous carrier;
    (c) passing a microcatheter intravascularly so that the microcatheter passes through the intravascular device into the target vascular site;
    (d) passing the embolization device through the microcatheter so that it emerges from the microcatheter into the target vascular site; and
    (e) passing saline solution through the microcatheter and into the vascular site to expand the embolizing element in situ substantially to fill the volume of the target vascular site while retaining the embolizing element on the carrier.

15. A method of embolizing a target vascular site having a defined volume, comprising the steps of:
    (a) deploying an intravascular device to a position in a blood vessel adjacent to a target vascular site;
    (b) providing a vascular embolization device comprising an expansible embolizing element non-releasably carried on a filamentous carrier;
    (c) passing a microcatheter intravascularly so that the microcatheter passes through the intravascular device into the target vascular site;
    (d) passing the embolization device through the microcatheter so that it emerges from the microcatheter into the target vascular site, while injecting a substantially non-aqueous fluid through the microcatheter to prevent hydration of the expansible elements within the microcatheter; and (e) expanding the embolizing element in situ substantially to fill the volume of the target vascular site while retaining the embolizing element on the carrier.

16. A method of embolizing a target vascular site having a defined volume, comprising the steps of:

(a) deploying an intravascular device to a position in a blood vessel adjacent to a target vascular site;

(b) visualizing the vascular site to determine at least an approximation of the volume of the vascular site;

(c) selecting a vascular embolization device comprising an expansible embolizing element non-releasably carried on a filamentous carrier and sized substantially to fill the volume of the vascular site when the embolizing element is expanded;

(d) passing a microcatheter intravascularly so that the microcatheter passes through the intravascular device into the target vascular site;

(e) passing the embolization device through the microcatheter so that it emerges from the microcatheter into the target vascular site; and (f) expanding the embolizing element in situ substantially to fill the volume of the target vascular site while retaining the embolizing element on the carrier.

17. A method for embolizing a target vascular site having a defined volume, comprising the steps of:

(a) passing a microcatheter intravascularly so that its distal end is introduced into a target vascular site;

(b) passing a vaso-occlusive device through the microcatheter into the target vascular site so that the vaso-occlusive device assumes a three-dimensional configuration that fills a portion of the volume of the target vascular site;

(c) providing a vascular embolization device comprising an expansible embolizing element non-releasably carried on a flexible filamentous carrier;

(d) passing the embolization device through the microcatheter so that it emerges from the distal end of the microcatheter into the target vascular site; and (e) passing saline solution through the microcatheter and into the vascular site to expand the embolizing element in situ substantially to fill remaining volume of the target vascular site while retaining the embolizing element on the carrier.

18. A method for embolizing a target vascular site having a defined volume, comprising the steps of:

(a) visualizing the vascular site to determine at least an approximation of the volume of the vascular site;

(b) during or subsequent to the step of visualizing, passing a microcatheter intravascularly so that its distal end is introduced into a target vascular site;

(c) passing a vaso-occlusive device through the microcatheter into the target vascular site so that the vaso-occlusive device assumes a three-dimensional configuration that fills a portion of the volume of the target vascular site;

(d) selecting a vascular embolization device comprising an expansible embolizing element non-releasably carried on a flexible filamentous carrier, the embolization device being sized substantially to fill the volume of the vascular site when the embolizing element is expanded;

(e) passing the embolization device through the microcatheter so that it emerges from the distal end of the microcatheter into the target vascular site; and (f) expanding the embolizing element in situ substantially to fill remaining volume of the target vascular site while retaining the embolizing element on the carrier.

19. A method for embolizing a target vascular site having a defined volume, comprising the steps of:

(a) passing a microcatheter intravascularly so that its distal end is introduced into a target vascular site;

(b) passing a vaso-occlusive device through the microcatheter into the target vascular site so that the vaso-occlusive device assumes a three-dimensional configuration that fills a portion of the volume of the target vascular site;

(c) providing a vascular embolization device comprising an expansible embolizing element non-releasably carried on a flexible filamentous carrier;

(d) passing the embolization device through the microcatheter so that it emerges from the distal end of the microcatheter into the target vascular site, while injecting a substantially non-aqueous fluid through the microcatheter to prevent hydration of the expansible elements within the microcatheter; and (e) expanding the embolizing element in situ substantially to fill remaining volume of the target vascular site while retaining the embolizing element on the carrier.

* * * * *